US006246895B1

(12) United States Patent
Plewes

(10) Patent No.: US 6,246,895 B1
(45) Date of Patent: Jun. 12, 2001

(54) IMAGING OF ULTRASONIC FIELDS WITH MRI

(75) Inventor: Donald B. Plewes, Toronto (CA)

(73) Assignee: Sunnybrook Health Science Centre, Toronto (CA)

(*) Notice: Subject to any disclaimer, the term of this patent is extended or adjusted under 35 U.S.C. 154(b) by 0 days.

(21) Appl. No.: 09/216,116

(22) Filed: Dec. 18, 1998

(51) Int. Cl.[7] .................................................. A61B 5/055
(52) U.S. Cl. ............................................ 600/410; 324/309
(58) Field of Search .................................. 600/410, 411, 600/412, 419; 324/306, 309

(56) References Cited

U.S. PATENT DOCUMENTS

| 5,711,300 | * | 1/1998 | Schneider et al. | 128/653.2 |
| 5,810,731 | * | 9/1998 | Sarvazyan et al. | 600/438 |
| 5,977,770 | * | 11/1999 | Ehman | 324/318 |
| 6,064,206 | * | 5/2000 | Van Vaals et al. | 324/312 |

OTHER PUBLICATIONS

*Magnetic Resonance Imaging Of Ultrasonic Fields*, Ultrasound in Med. & Biol., vol. 24, No. 1, pp. 137–142, 1998; C.L. Walker, F.S. Foster & D.B. Plewes, Jan. '98.

*Oscillatory Flow in the Cochlea Visualized by a Magnetic Resonance Imaging Technique*, Proc. Natl. Acad. Sci, USA, vol. 90, pp. 1595–1598, Feb. 1993, Winfried Denk, et al.

*Magnetic Resonance Elastography by Direct Visualization of Propagating Acoustic Strain Waves*, Science, vol. 269, pp. 1854–1857, Sep. 29, 1995, R. Muthupillai, et al.

*Magnetic Resonance Imaging in the Presence of Medical Waves*, Spectroscopy Letters, 24(1), 55–67 (1991), Czeslaw j. Lewa.

*Viscoelastic Property Detection by Elastic Displacement NMR Measurements*, JMRI 1996; 6:652–656, Czeslaw J. Lewa, et al.

* cited by examiner

Primary Examiner—Peter Vo
Assistant Examiner—Shawna J. Shaw
(74) Attorney, Agent, or Firm—Quarles & Brady, LLP; Christan G. Cabou

(57) ABSTRACT

An MRI system is employed to produce an image of an ultrasonic wave propagating through tissue or the like. An imaging pulse sequence used to acquire the image data is performed in synchronism with the operation of an ultrasonic transducer, and reconstructed phase images measure the motion of excited spins. Physical parameters of the acoustic field such as acoustic pressure, acoustic intensity and wave number may be calculated and imaged. Non-linear propagation characteristics of the acoustic field are also measured and imaged.

4 Claims, 4 Drawing Sheets

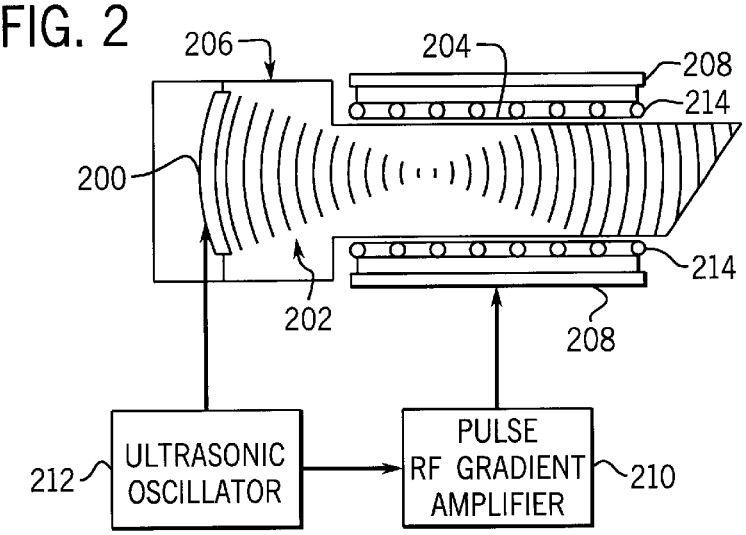
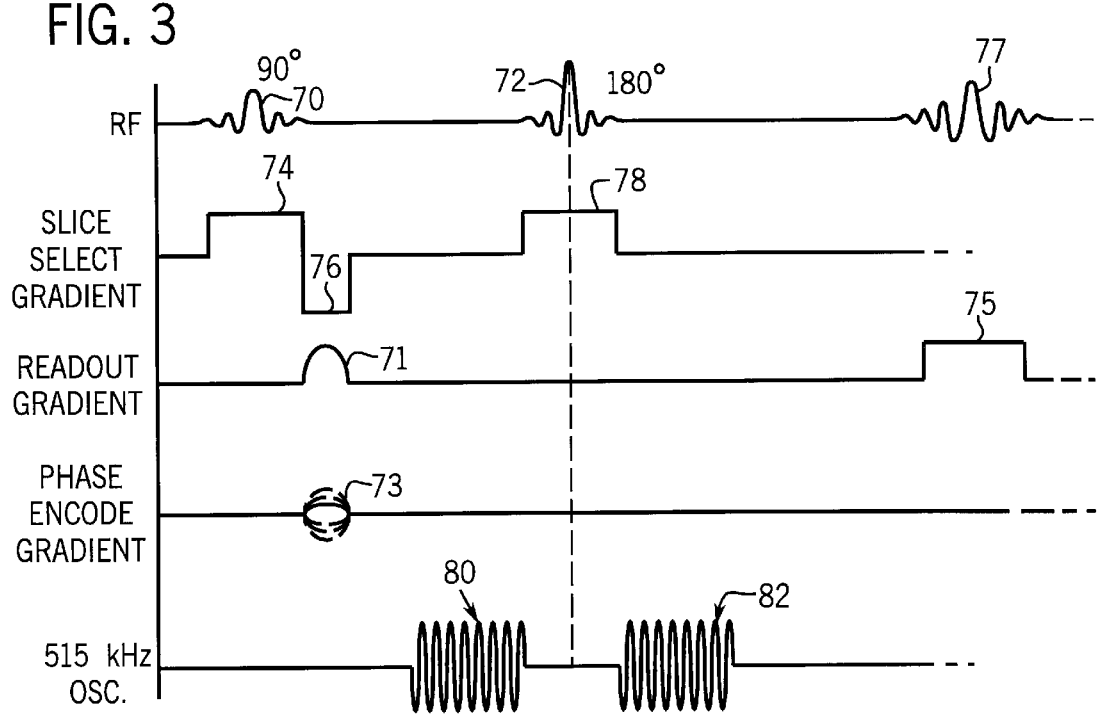

IMAGING OF ULTRASONIC FIELDS WITH MRI

BACKGROUND OF THE INVENTION

The field of the invention is nuclear magnetic resonance imaging methods and systems. More particularly, the invention relates to the Imaging of ultrasonic fields using a magnetic resonance imaging (MRI) system.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Nuclear magnetic resonance signals can be influenced by motion through the application of a magnetic field gradient superimposed on the static, uniform magnetic field that is used for spin polarization (Hahn E L, Detection of c-water motion by nuclear precession, J Geo-phys Respectively 1960;65:766–777). This concept has been used with proton MRI to image fluid flow (Frayne R, Steinmann D A, Ethier C R, Rutt B K, Accuracy of MR phase contrast velocity measurements for unsteady flow, J Magn. Reson. Imaging 1995;5:428–431), brain (Enzmann D R, Pelc N J, Brain motion: measurement with phase contrast MR imaging, Radiology 1992;185:653–600) and muscle (Pelc L R, Sayre J, Yun K, Castro L J, Herfkens R J, Miller D C, Pelc N J, Evaluation of myocardial motion tracking with cine-phase contrast magnetic resonance imaging, Invest Radiol 1994;29:1038–1042) tissue motion, as well as the measurement of cardiac tissue strain (Wedeen V J, Magnetic resonance imaging of myocardial kinematics, Technique to detect, localize, and quantify the strain rates of the active human myocardium, Magn Reson Med 1992;27:52–67). Several authors have used oscillating magnetic field gradients to detect oscillatory fluid flow or viscoelastic tissue motion. Specifically, acoustic oscillatory fluid flow in the rat cochlea (Denk W, Keolian R M, Ogawa S. Jelinski L W, Oscillatory flow in the cochlea visualized by a magnetic resonance imaging technique, Proc Natl Acad Sci 1993; 90:1595–1598) has been demonstrated at frequencies up to 4.6 kHz. Similarly, the viscoelastic properties of tissue have been measured by monitoring the wave velocity of slow (<10 m/s), low-frequency shear waves (<1.1 kHz) (Lewa C J, de Certaines J D, Viscoelastic property detection by elastic displacement NMR measurements, J Magn Reson Imaging 1996; 6:652–656; Muthupillai R, Lomas D J, Rossman P J, Greenleaf J F, Manduca A, Ehman R L, Magnetic resonance elastography by direct visualization of propagation acoustic strain waves, Science 1995; 269:1854–1857; Muthupillai R, Rossman P J, Lomas D J, Greenleaf J F, Riederer S J, Ehman R L, Magnetic resonance imaging of transverse acoustic strain waves, Magn Reson Med 1996; 36:266–274) generated by mechanical stimulation. In these cases, the oscillation frequency was limited to a few kHz, with motion amplitudes ranging from 200–1000 nanometers.

The concept of motion-sensitized MRI arises from the fact that the proton Larmor frequency is proportional to the local magnetic field. By using a magnetic field gradient, in addition to a uniform polarizing field, the resultant distribution of frequencies encodes the spatial distribution of spin density. Similarly, when spins are moving in the presence of this gradient, the phase of the spins indicates the history of spin location in their movement through a gradient.

More specifically, the phase of transverse magnetization is influenced by its location and the presence of an applied magnetic field gradient. As described in more detail below, the motion of a spin can be measured by this phase depending on the nature of the motion, and the duration, waveform and amplitude of the applied magnetic field gradient.

The application of ultrasound (US) in the medical field is widespread and growing rapidly. The success of these diverse applications is largely determined by the ability to craft specific acoustical field patterns within tissue in a controlled and predictable fashion. The ability to observe a field pattern in acoustically heterogeneous tissues is important to understand the effect of phase aberrations on spatial resolution in imaging application, and on the deposition of thermal energy in high-intensity focused ultrasound (HIFU) applications. Validation of US field patterns in homogeneous media can be predicted on the basis of classical diffraction theory (Hunt J W, Arditi M, Foster F S, Ultrasound transducers for pulse-echo medical imaging, IEEE Trans Biomed Eng 1983; BME-30:453–481) and verified with invasive sensors (Schafer M E, Lewin P A, Computerized system for measuring the acoustic output from diagnostic ultrasound equipment, IEEE Trans Ultrason Ferroelectr Freq Control 1988;35:102–109; Fry W S, Fry R B, Determination of absolute sound levels and acoustic absorption by thermocouple probes, J Acoust Soc Am 1954;26:294–317) implanted within the tissue. In transparent media, direct observation of the acoustic field can be achieved with optical methods (Raman C V, Nath N S, The diffraction of light by high frequency ultrasonic waves, Proc Indian Acad Sci 1935;2:406–412; Breazeale M A, Heideman E A, Optical methods for measurement of sound pressure in liquids, J Acoust Soc Am 1959;31:24–33) or optical diffraction tomography (Pitts T, Greenleaf J, Lu J Y, Kinnick R, Tomographic schlieren imaging for measurement of beam pressure and intensity, IEEE Ultrasonic Symposium 1994, page 1665). However, these techniques collectively suffer from being either local, invasive, or not applicable to human tissues that are neither transparent nor homogeneous. The ability to provide an accurate non-invasive means, of visualizing the propagation of longitudinal ultrasonic waves in tissue and to quantify its intensity distribution would fill an important need in the development of optimized US therapeutic and imaging strategies.

In current practice, the detection of non-linear US processes is only archived by the use of invasive high bandwidth or tuned hydrophones which measure higher-order harmonics. However, in order to understand the details of shock formation and dissipation of US in heterogeneous tissue, an image of the presence of higher-order motions is needed. While the simultaneous use of multiple hydrophones throughout the media can approximate this distribution it is cumbersome in tissue and will likely alter the US field itself.

SUMMARY OF THE INVENTION

The present invention is a method for using an MRI system to image the minute particle displacements that accompany propagating ultrasonic waves in a media and to thereby measure acoustic parameters of the acoustic field as well as nonlinear propagation of the acoustic field in the media which can cause cavitation or overheating of tissues. More particularly, the method includes acquiring an MR image of the media in which the acoustic wave is propagating using a pulse sequence in which an oscillating gradient field is synchronously applied to measure the displacement of spins caused by the acoustic wave. Spin displacement is indicated by the phase of the acquired MR image and using the resulting displacement image, further images indicative of acoustic parameters can be calculated. These acoustic parameters include acoustic pressure, acoustic intensity, wave number and the speed of sound in the media which can be determined from the wave number.

The acoustic field measurements using an MRI system according to the present invention are direct and provide an accurate measure of particle displacement from very simple interactions with pulsed magnetic field gradients which in turn generate a detectable phase variation in the MRI signal. This phase variation is related to the particle displacement in a very straightforward manner which is dependent on basic physical constants (gyromagnetic ratio of protons), imaging parameters (oscillating gradient duration and frequency) and the oscillating gradient amplitude. Together these properties can be used to make a direct measure of particle displacement from which ultrasound intensity and pressure can be determined at specific frequencies based on other constants, which are the density of the media and the speed of sound. The density of the media can be measured a-priori while the speed of sound in the media can be measured from the acquired MR image based on the known frequency of the acoustic wave source.

Another aspect of the present invention is the imaging of non-linear effects of acoustic wave propagation. The frequency of the synchronous oscillating gradient may be changed to measure particle displacement produced by harmonics of the transducer base frequency. This may be performed by repeating the MRI measurement at different synchronous gradient frequencies and combining the resulting images, or a composite synchronous gradient may be used in one measurement which contains the base frequency and selected harmonics. In either case, the resulting image enables a quantitative, direct visualization of the magnitude and distribution of all non-linear effects in the US field.

BRIEF DESCRIPTION OF THE DRAWINGS

FIG. 2 is a pictorial representation of the apparatus used in the MRI system of FIG. 1 to practice the preferred embodiment of the invention; and FIGS. 3, 5 and 6 are graphic representations of a preferred NMR pulse sequence performed by the MRI system of FIG. 1 to practice the present invention.

DESCRIPTION OF THE PREFERRED EMBODIMENT

Figure 1:
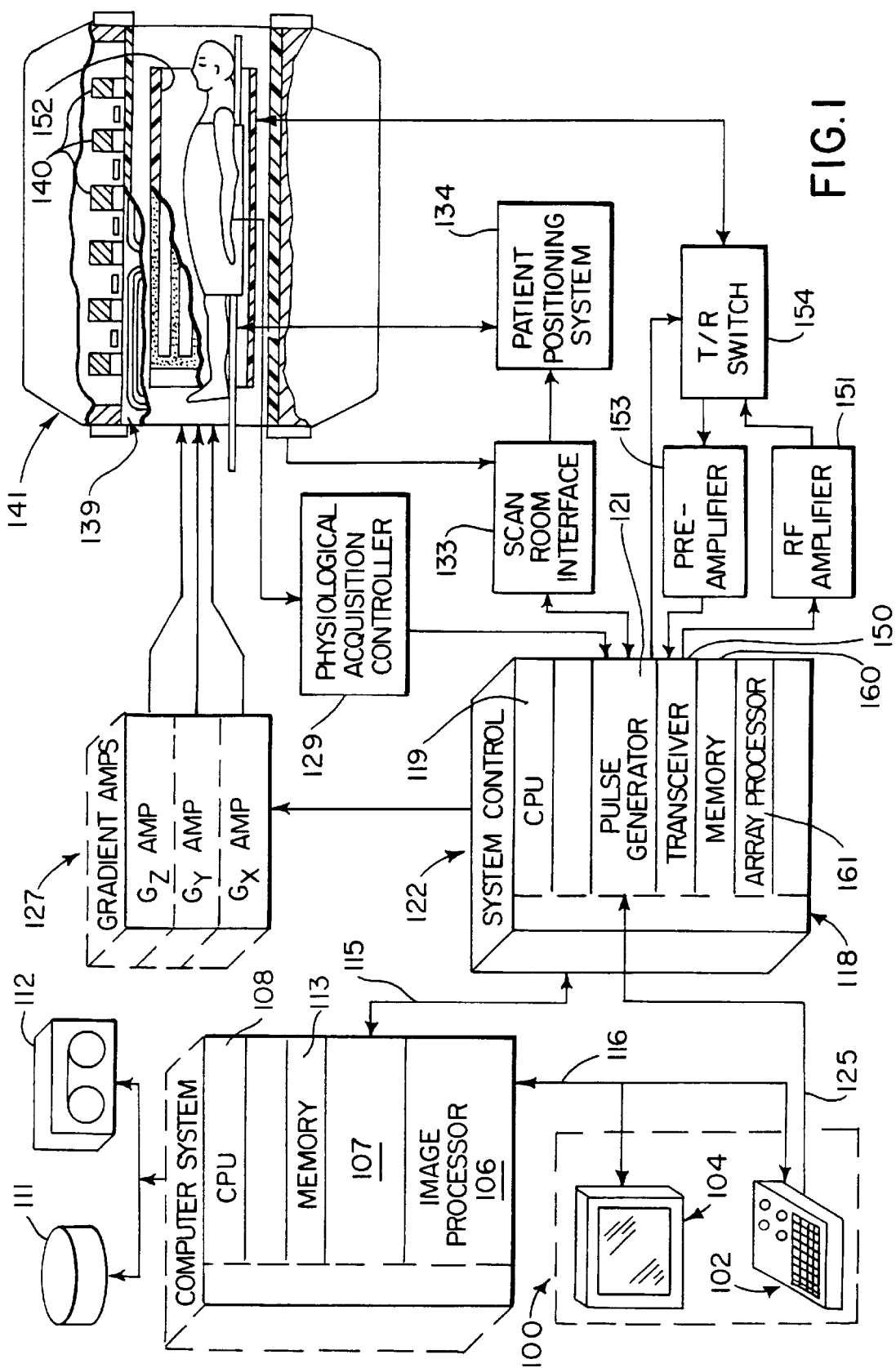
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane 118. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. As will be described below, a local gradient coil is used in the preferred embodiment and is separately driven in synchronism with an applied ultrasonic wave.

The gradient coil assembly 139 forms part of a magnet assembly 141 which includes a polarizing magnet 140 and a whole-body RF coil 152. In the preferred embodiment the whole-body RF coil 152 is disabled and a local RF coil described in more detail below is used for both transmission and reception. A transceiver module 150 in the system control 122 produces RF pulses which are amplified by an RF amplifier 151 and coupled to the local RF coil by a transmit/receive switch 154. The resulting NMR signals radiated by the excited nuclei are sensed by the same local RF coil and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the RF coil during the transmit mode and to connect the preamplifier 153 during the receive mode.

The NMR signals picked up by the RF coil are digitized by the transceiver module 150 and transferred to a memory module 160 in the system control 122. When the scan is completed and an entire array of data has been acquired in the memory module 160, an array processor 161 operates to Fourier transform the data into an array of image data. To practice the present invention a phase image is produced using this image data rather than the usual magnitude image. Each pixel in the phase image is calculated by taking the arctangent of the ratio of the I and Q values at each location in the image data array. This phase image is conveyed through the serial link 115 to the computer system 107 where it is stored in the disk memory 111. In response to commands received from the operator console 100, this phase image may be archived on the tape drive 112, or it may be further processed by the image processor 106 and conveyed to the operator console 100 and presented on the display 104.

For a more detailed description of the transceiver 150, reference is made to U.S. Pat. Nos. 4,952,877 and 4,992,736 which are incorporated herein by reference.

Referring particularly to FIG. 2, an experimental apparatus was constructed and placed in the bore of the magnet assembly 141 in place of the patient shown in FIG. 1. This experimental apparatus includes a 5 cm diameter ultrasonic transducer 200 which produces a focused ultrasonic beam 202 having a frequency of 515 kHz. The ultrasonic beam 202 is focused at a depth of 10 cm within a 3 cm diameter cylindrical chamber 204 containing a tissue-equivalent agar mixture. The transducer 200 is mounted in a chamber 206 at one end of the cylindrical chamber 204 and the far end of the cylindrical chamber 204 is angled and roughened to scatter and absorb the ultrasonic waves after one passage through the cylindrical cavity. This eliminates wave reflections.

An oil-cooled, resonant gradient coil 208 is disposed around the cylindrical chamber 204 and it is wound to produce a magnetic field gradient along the direction of the propagating ultrasonic wave 202. The resonant gradient coil 208 is tuned to operate at the 515 kHz ultrasonic frequency and it is driven by a separate pulsed RF gradient amplifier 210 to produce a maximum gradient strength of 0.40 T/m at the focus of the beam 202, with a gradient full-width half-maximum of 5.6 cm. MR measurements of the gradient field distribution were used to correct spatial variations in gradient field strength and to provide a uniform displacement sensitivity over the imaging volume within the cylindrical chamber 204. The pulsed RF gradient amplifier 210 is driven in synchronism with the ultrasonic transducer 200 by an ultrasonic oscillator 212. The ultrasonic oscillator is in turn operated by the pulse generator module 121 on the MRI system. As will be explained in more detail below, the ultrasonic beam 202 and the phase-locked gradient oscillations are applied in synchronism with an imaging pulse sequence produced by the pulse generator module 121.

To enhance the signal-to-noise ratio of the acquired image a local RF coil 214 is disposed between the cylindrical chamber 204 and the local gradient coil 208. In the preferred embodiment a guadrature coil is employed, although other coils such as "bird cage" coils may be used for this purpose. Any local coil which couples well with the imaging region inside the cylindrical chamber 204 may be used.

Referring particularly to FIG. 3, while many different pulse sequences may be used to practice the present invention, the preferred pulse sequence is a spin echo pulse sequence in which a 90° rf excitation pulse 70 is applied, followed by a 180° rf refocusing pulse 72. Slice select gradient pulses 74 and 78 are applied concurrently with the respective rf pulses 70 and 72 to limit the region of excitation to a slab passing along the center line of the cylindrical chamber 204. A rephasing slice select gradient pulse 76 is applied after the 90° RF excitation along with a readout gradient dephasing pulse 71 and a phase encoding gradient pulse 73. As is well known in the art, the pulse sequence is repeated many times (e.g. 64, 128 or 254) during a scan and this phase encoding pulse 73 is stepped through a set of discrete values. At the completion of each pulse sequence, an NMR echo signal 77 is acquired in the presence of a readout gradient pulse 75 and at the completion of the scan, therefore, an array of k-space data has been acquired. As indicated above, image data is produced by performing a two-dimensional Fourier transformation of this acquired k-space data array and then a phase image is produced by calculating the phase of the complex signal at each pixel:

$$\phi = TAN^{-1} Q/I$$

where I and Q are in-phase and quadrature components of the complex signal.

The preferred embodiment of the present invention is implemented by enabling the ultrasonic oscillator 212 for (N) cycles before the refocusing pulse 72, as indicated at 80, and for (N) cycles after the refocusing pulse 72, as indicated at 82. As a general rule, the number of cycles (N) is set to the maximum number possible that can be played out during the pulse sequence echo time (TE). As will be described in more detail below, the phase of the oscillations 82 after the refocusing pulse 72 is produced is reversed 180° such that the effect on the phase of the NMR echo signal will be cumulative. A second phase image is then acquired without application of the ultrasonic beam 202. This serves as a reference phase image which is subtracted from the first phase image to yield a final phase image. The subtraction of the reference phase image suppresses all phase variations in the imaging volume which are unrelated to the ultrasonic beam 202.

Figure 5:
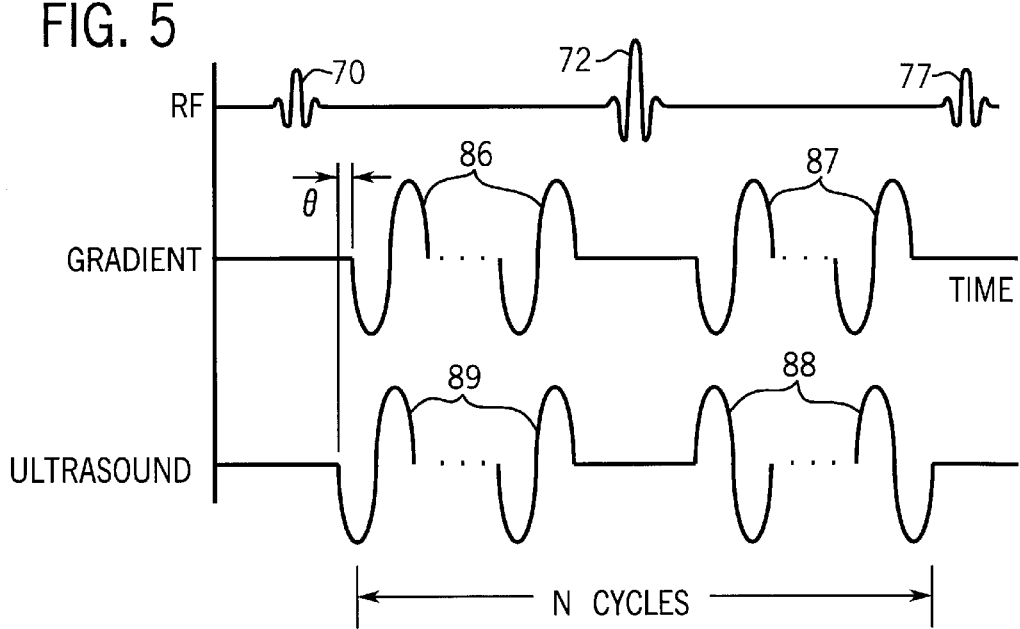
Figure 6:
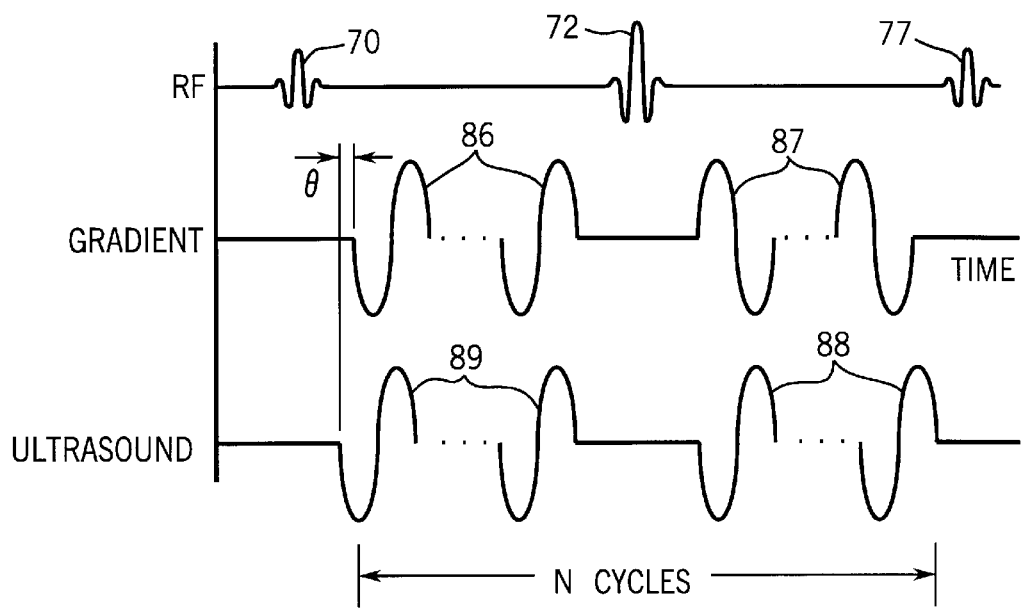

As indicated above, the phase of the US excitation relative to the phase of the synchronous oscillating gradient waveform is shifted by 180° after the RF refocusing pulse 72 is produced. This is done so that the effect on phase of the acquired echo signal 77 will continue to accumulate after the RF refocusing pulse 72. This can be done in two ways. As shown in FIG. 5, the phase of the oscillating gradient before 86 and after 87 the RF refocusing pulse 72 can be kept the same. In this case, the phase of the ultrasound excitation 88 after the RF refocusing pulse 72 is shifted 180° in phase relative to the ultrasound excitation 89 applied before the RF refocusing pulse 72. In the alternative as shown in FIG. 6, the phase of the synchronous oscillating gradient 87 after the RF refocusing pulse 72 is shifted 180° relative to the gradient 86, and the phase of the ultrasound excitation 88 and 89 remains unchanged.

An alternative embodiment for subtracting the two image sets, is to apply the US for both sequences, but invert the phase of the oscillating synchronous gradient waveform between the two acquisitions. This approach is used for phase contrast motion encoding in most MR imaging systems. This has the advantage of improving the SNR of the subtracted phase images by a factor of two since the phase changes caused by the US field are added while other phase changes are canceled.

Unlike physiologic motion, the timing and phase of the US motion can be controlled. Thus, a third and unique approach to acquire the first MR image with the oscillating gradient and US phase in-phase as shown in FIG. 3, followed by a second acquisition in which the phase of the US is inverted. Subtraction of these two MR data sets results in a phase distribution which reports particle motion caused by the US field, while canceling any constant phase errors which occur in both imaging sequences. As in the case of motion phase swapping, this approach also enjoys the advantage of an increase in SNR due to the fact that both motion encoding images are acquired in the presence of US motion.

The resultant phase image is corrected for variations in the gradient magnitude throughout the imaging volume.

The phase of transverse magnetization, φ, in the presence of a magnetic field gradient is determined by:

$$\phi(r) = \gamma \int G(t) \cdot r(t) dt \quad (1)$$

where γ is the gyromagnetic ratio for protons, r(t) describes the temporal dependence of the spin position, and G(t) is the waveform of the applied gradient. If we consider the spins at equilibrium position $r_o$ to be undergoing harmonic motion of amplitude $\xi_o$ arising from a plane ultrasound wave with angular frequency ω and wave number $k_r$, the displacement can be written as:

$$\xi(r,t) = r_o + \xi_o \sin(\omega t - k_r \cdot r). \quad (2)$$

By applying an oscillating gradient $G = G_0 \cos(\theta - \omega t)$ for a duration T seconds and, substituting into Eq. (1), we generate a phase distribution throughout the MR image given by:

$$\phi(r, \theta) = \frac{\gamma G_0 \xi_0}{2} \left\{ T\sin(\theta - k_r \cdot r) - \frac{\sin(2\omega T)\sin(\theta - k_r \cdot r)}{2\omega} + \frac{\sin^2(\omega T)\cos(\theta - k_r \cdot r)}{\omega} \right\} \quad (3)$$

Typically T will be several orders of magnitude larger than ½ω so that the second and third terms of this expression can be ignored. Recasting it in terms of ultrasound induced displacement amplitude we have:

$$\xi_0 \sin(\theta - k_r \cdot r) = \frac{2\phi(r, \theta)}{\gamma G_0 T} \quad (4)$$

where T is the duration of the waveforms 80 and 82. Thus, the spatial distribution of phase in the reconstructed phase image reports the local ultrasound-induced displacement amplitude both as a function of location r and at time dictated by θ/ω. By generating multiple images while sweeping this parameter over an ultrasonic cycle, the temporal evolution of the ultrasonic field can be observed. The measured displacement amplitude ($\xi_o$) can be used to estimate the spatial distribution of acoustic pressure amplitude p, and acoustic intensity I according to:

$$p(r,\theta) = \rho c \omega \xi(r,\theta) \quad (5)$$

$$I(r, \theta) = \frac{1}{2} \rho c \omega^2 \xi(r, \theta)^2 \quad (6)$$

where c is the speed of sound in a medium with density ρ. The ultrasonic wave speed can be inferred from previous measurements or it can be determined directly from the MR phase image, using the measured wave number ($k_r$), and the known ultrasound frequency. Note that the determination of the absolute ultrasonic displacement, pressure and intensity depends only on a fundamental constant γ, knowledge of the applied magnetic field gradient G and its duration T. Thus, the accuracy of the approach is guaranteed without reference to external standards.

To insure accuracy of the measurements the above procedure is repeated with the oscillating gradient applied along the respective x, y and z axes. While the majority of motion occurs along the direction of US propagation, tissue motion may have components in other directions depending on the orientation of the US transducer, its focusing pattern and the scattering that occurs within the tissue. Six separate measurements are thus required for each acquired view, two measurements along each gradient axis. This number can be reduced to four measurements, however, if a single reference measurement is subtracted from each of the gradient direction measurements.

Figure 4:
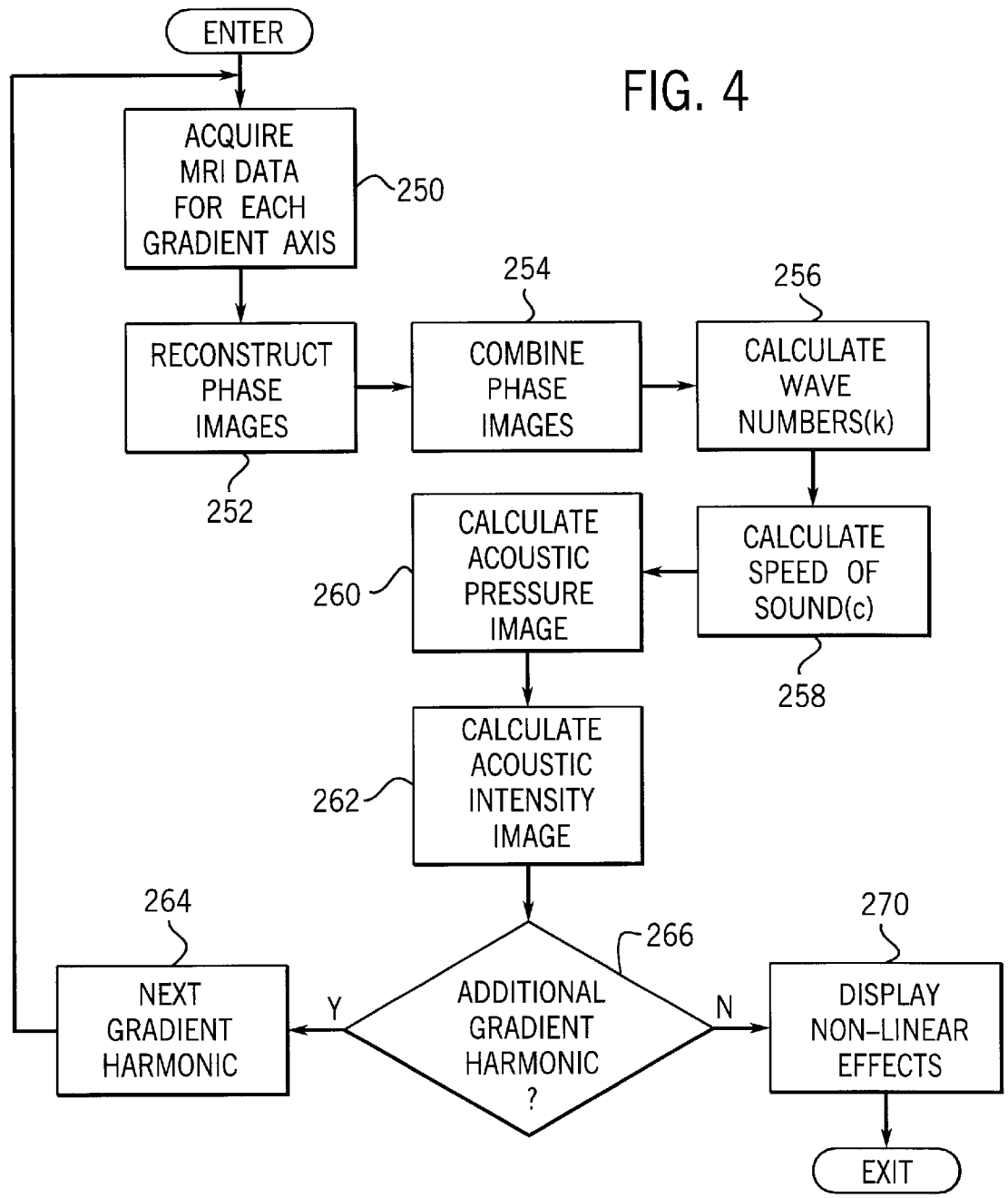
FIG. 4 is a flow chart of the preferred method for practicing the invention on the MRI system of FIG. 11.

Referring particularly to FIG. 4, the preferred method for implementing the inventions produces pressure and intensity images of the US wave propagating through the media, and an image which shows the higher-order motions produced by non-linear effects. The first step as indicated at process block 250 is to acquire the synchronous motion images along each of the x, y and z gradient axis. The pulse sequence of FIG. 3 may be employed in the MRI system of FIG. 1 to produce three corresponding k-space image data sets. Three images are reconstructed from these k-space data sets by performing a 2D fast Fourier transformation and calculating the phase at each pixel location from the I and Q values as discussed above and indicated at process block 252. In the alternative, a 3D spin echo pulse sequence may be employed, in which case the three acquired images are reconstructed by performing a 3D fast Fourier transform.

As indicated at process block 254 the three, phase images are combined to produce a 3D displacement image. This displacement image indicates the amount of movement at each pixel along each gradient axis, and from this information the direction of wave propagation can be determined at each pixel. The displacement ($\xi_0$) indicated at each pixel can be used to calculate the local acoustic pressure (p) and the local acoustic intensity (I) according to equations (5) and (6) above. However, the speed of sound (c) and the medium density (ρ) are required for these calculations.

The speed of sound can be estimated (e.g. 1500 meters/sec) and the density of the tissue in the region of interest can be measured separately. In the preferred embodiment, however, the speed of sound in the media is measured from the displacement image. As indicated at process block 256, the first step in this procedure is to calculate the wave number K of the displacements indicated in the displacement image. The displacements oscillate in amplitude in space and the objective is to calculate the instantaneous spatial frequency of these oscillations in the region of interest. This can be accomplished in a number of ways, but in the preferred embodiment a wave number image is produced by filtering the displacement image with a filter such as those described by Boashas B, "Estimating and Interpreting the Instantaneous Frequency of a Signal, Parts 1 and 2", *Proceedings of the IEEE,* 80(4) 520–568, 1992, and Knutsson H, Westin J, Granland G, "Proceedings of the IEEE International conference on Imaging Processing-94," *IEEE Computer Society Press,* Los Alamitos, Calif. ed. 1, 1994, p36. If the region of interest is not too small, and the speed of sound is relatively constant, the Fourier transform of the displacements along the direction of wave propagation will also yield an estimate of k at the Fourier transform peak value. As indicated at process block 258, the speed of sound (c) can then by calculated from the k number:

$$c = \frac{\omega}{|K|} = \frac{\omega}{\sqrt{K_x^2 + K_y^2 + K_z^2}}$$

where $K_x$, $K_y$ and $K_z$ are measured from the three-dimensional displacement images.

All of the information is now available to calculate an acoustic pressure image as indicated at process block 260. The pressure is calculated according to equation (5) above using the displacement amplitude ($\xi$) at each pixel, the speed of sound (c), the density ($\rho$) and the known transducer frequency ($\omega$). Similarly an acoustic intensity image is calculated at process block 262 using these same values and equation (6) above. The full three dimensional distribution of the complex US wave can thus be measured and imaged. This then allows the direct quantitative assessment of the absolute magnitude of the three dimensional US field in tissue without resorting to calibrated instrumentation. Furthermore, the method allows images of the US field to be obtained at arbitrary times relative to the US source excitation. Thus, 'snapshots' of the US wave can be obtained at varying times throughout a single US cycle which allows the visualization of the dynamics of wave propagation and scattering within tissue.

When the power to an US transducer is small, the resulting pressure variations in the media are small and the wave propagation is considered to be linear. In this situation, the propagation speed of the US wave is constant. However, as the excitation power to the transducer increases, the resultant pressure variations within the media increase and its propagation becomes non-linear. With high pressures, the density of the media increases slightly with a corresponding increase in the local speed of sound. As the media density variations are distributed over a wavelength of the field, this indicates that the speed of sound is dependent on position within the waveform. This effect results in a waveform distortion which gradually increases with propagation distance from the US source. The net result is that the region of peak pressure propagates at a slightly higher velocity and overtakes the region of rarefaction in a process known as 'steepening'. After a specified distance, the shape of the acoustic waveform becomes severely distorted and approaches a sawtooth waveform rather than its original sinusoidal wave shape. This non-linear process leads to the gradual formation of a shock front as characterized by a pressure discontinuity at the steepest portion of the sawtooth. After the shock is formed, further propagation will attenuate the wave through viscous losses while maintaining its sawtooth profile. The ability to visualize these non-linear processes in tissue has important implications for US exposimetry where power levels of non-linear exposures can be of concern. Furthermore, recent innovations in US imaging methods are to some degree based on non-linear interactions which heretofore have not be easily analyzed. The present invention enables these non-linear effects to be measured and imaged by producing additional acoustic pressure images at synchronous gradient frequencies at harmonics of the acoustic transducer frequency ($\omega$).

Referring again to FIG. 4, the entire process described above is repeated after changing the frequency of the applied synchronous gradient as indicated at process block 264. The synchronous gradient is operated at a multiple of the transducer frequency ($\omega$) during each repeat of the process. Only the first few harmonics need be measured because the amplitudes of higher harmonics become insignificant with respect to the fundamental frequency ($\omega$). When the last harmonic has been acquired as determined at decision block 266, images depicting the non-linear effects on the acoustic wave are produced at process block 270.

The measured non-linear effects can be displayed in a number of different ways. First the growth of the higher order harmonics with distance from the transducer can be visualized as a map of each harmonic. In addition, these harmonics can be added together as Fourier components using the measured amplitude and phase information of each harmonic. This results in an image of the actual pressure distribution throughout the field and allows direct visualization of the sawtooth-like nature of the acoustic pressure field. By this means the exact nature of the non-linear mechanics of the US propagation can be understood in heterogeneous tissue.

One difficulty with the above approach is the amount of time needed to complete the data acquisition of the multiple harmonics. An alternative method is to measure using a synchronous gradient waveform which includes all the harmonics of interest which are then applied simultaneously. In this case, the synchronous gradient waveform is the superposition of the harmonics of interest so that the gradient apparatus needs to be tuned to oscillate at multiple frequencies which exactly match the harmonics of the non-linear US field. This results in an image of displacement reflecting gradient amplitudes at each frequency. The contributions of any single frequency can be easily achieved by post-processing the image data with a Fourier filter at the desired frequency for each of the harmonics, normalized against the gradient amplitude. The advantage of such a method is the reduction in the scan time needed to record the multiple harmonics as all the harmonics are recorded in a single MR acquisition.

The images produced by the present invention can also be used to probe the scattering and reflectance properties of ultrasound waves at various interfaces within tissue. For example, when US in a media of acoustic impedance $Z_1$ is directed toward a second media which is planar and orthogonal to the direction of wave propagation with impedance $Z_2$ the pressure reflection coefficient from the interface is given by $R=(Z_2-Z_1)/(Z_1+Z_2)$. In this case, the transmission coefficient through the interface is given by 1–R. When the orientation of the interface with the incident US wave is not normal, the expression becomes more complex. MR imaging of the US pressure field allows direct measurement of the characteristics of such interfaces and their respective acoustic impedances. Again, in the simple case of a normally oriented interface, the field can be measured both in terms of its amplitude and relative phase for various points throughout the US period in the vicinity of the interface. For a plane wave propagating toward the interface along the x direction a simple model for the pressure field before the interface is given by $P_i$ cos(t–Kx)+R $P_i$ cos(t+Kx), where Pi is the pressure amplitude incident on the interface. Similarly, the field beyond the interface is given by (1–R)$P_i$ cos(t–Kx). By collecting images from the two regions throughout various points in the US cycle, it is possible to fit the data to these models, thereby determining the reflection coefficient between the two boundaries. This technique may be applied in situations of different geometry whereby different models are used; however, the concept remains the same.

What is claimed is:

1. A method for imaging the properties of ultrasound waves at a boundary within tissue using a transducer operating at a base frequency, the steps comprising:
   a) acquiring magnetic resonance image data from the tissue using a pulse sequence that employs an oscillating gradient that is synchronized with the operation of the transducer;

b) reconstructing an image from the acquired image data which indicates the phase of spin magnetization produced by the oscillating gradient; and c) producing an image from the reconstructed image that quantitatively indicates a physical parameter of the acoustic field on both sides of the boundary; and d) calculating a reflectance property of the boundary from the indicated physical parameter.

2. The method as recited in claim 1 in which the physical parameter is acoustic pressure and the reflectance property is the reflection coefficient.

3. The method as recited in claim 1 in which steps a) and b) are repeated with an oscillating gradient oriented in a different direction and step c) includes combining the reconstructed images to provide a two-dimensional indication of the physical parameter.

4. The method as recited in claim 1 in which steps a) and b) are performed three times with three respective orthogonal oscillating gradients and step c) includes combining the three reconstructed images to provide a three-dimensional indication of the physical parameter.

* * * * *